US00RE49935E

(19) United States
(12) Reissued Patent
Zhong et al.

(10) Patent Number: US RE49,935 E
(45) Date of Reissued Patent: Apr. 23, 2024

(54) CRYSTALLINE POLYMORPHS OF BENFOTIAMINE, PROCESS FOR PREPARATION AND ITS USE THEREOF

(71) Applicant: Shanghai Raising Pharmaceutical Co., Ltd., Shanghai (CN)

(72) Inventors: Chunjiu Zhong, Shanghai (CN); Yinhua He, Shanghai (CN); Xuefeng Mei, Shanghai (CN); Huan Zhang, Shanghai (CN)

(73) Assignee: SHANGHAI RAISING PHARMACEUTICAL CO., LTD., Shanghai (CN)

(21) Appl. No.: 17/666,352

(22) Filed: Feb. 7, 2022

Related U.S. Patent Documents

Reissue of:
(64) Patent No.: 9,718,846
Issued: Aug. 1, 2017
Appl. No.: 14/432,079
PCT Filed: Oct. 31, 2012
PCT No.: PCT/CN2012/083898
§ 371 (c)(1),
(2) Date: Oct. 18, 2015
PCT Pub. No.: WO2014/059702
PCT Pub. Date: Apr. 24, 2014

(30) Foreign Application Priority Data

Oct. 17, 2012 (CN) ..... 201210395556.6

(51) Int. Cl.
*C07F 9/6512* (2006.01)
*A61K 31/675* (2006.01)

(52) U.S. Cl.
CPC ..... *C07F 9/6512* (2013.01); *A61K 31/675* (2013.01)

(58) Field of Classification Search
CPC ..... C07F 9/6512; A61K 31/675; A61P 3/00; A61P 3/02; A61P 3/10; A61P 25/18; A61P 25/28
See application file for complete search history.

(56) References Cited

U.S. PATENT DOCUMENTS 3,064,000 A 11/1962 Kaisha

FOREIGN PATENT DOCUMENTS

DE 1130811 B 6/1962
GB 896089 5/1962
(Continued)

OTHER PUBLICATIONS

I. Akira et. al., 82 Yakugaku Zasshi, 883-888 (1962).*
(Continued)

*Primary Examiner* — Alan D Diamond
(74) *Attorney, Agent, or Firm* — BakerHostetler

(57) ABSTRACT

The present invention is directed to crystalline polymorphs of benfotiamine, its methods of preparation and its use thereof. Five crystalline polymorphs of benfotiamine are designated as crystalline forms A, B, C, D and E, and may be distinguished by their respective patterns of X-ray powder diffraction (XRPD), differential scanning calorimetry (DSC), infrared spectroscopy (IR), raman spectroscopy, moreover by their diverse preparing process. The crystalline polymorphs of the present invention are useful as they act in treating Vitamin B1 deficiency, metabolic disorders, mental illness and disorders, diabetes complications, neurodegerative diseases. Further the present invention is a process for preparing and transforming diverse crystalline form of benfotiamine through different synthesis routes and varied solvents and combinations. The crystalline polymorphs of the present invention are basically pure. The present invention not only provides new crystalline forms of benfotiamine, but also provides its new solvates, especially hydrates.

24 Claims, 11 Drawing Sheets

(56) References Cited

FOREIGN PATENT DOCUMENTS

| | | | |
|---|---|---|---|
| JP | 37-11037 | B | 8/1962 |
| JP | 37-13483 | B | 9/1962 |
| JP | 37-13484 | B | 9/1962 |
| JP | 37-16042 | | 10/1962 |
| JP | 37-16042 | B | 10/1962 |
| JP | H10-053526 | A | 2/1998 |
| JP | 2006-008576 | A | 1/2006 |

OTHER PUBLICATIONS

English Translation of I. Akira et. al., 82 Yakugaku Zasshi, 883-888 (1962).*
Solid State Characterization of Pharmaceuticals 427-450 (R.A. Storey et al., eds., 2011).*
Asai et al., "A synthesis method of S-Benzoylthiamine O-Monophosphate", Takamine Kenkyujo Nenpo, 1961, vol. 13, pp. 45-47.
Caira, "Crystalline Polymorphism of Organic Compounds" Topics in Current Chemistry, 1998, No. 198, pp. 163-208.
Chinese Patent Application No. 201210395556.6: First Office Action dated Nov. 2, 2014, 12 pages.
European Patent Application No. 12886858.5 — 1451/2918593: Search Report dated Jul. 22, 2016, 7 pages.
International Patent Application No. PCT/CN2012/083898: International Search Report dated Jul. 25, 2013, 20 pages.
Ito et al., "Research on Vitamin B1 Phosphate ester (No. 6),the crystalline form and formation of S-Benzoylthiamine O-Monophosphate", Takamine Kenkyusho Nenpo, 1962, vol. 14, pp. 64-66.
Ito et al., "Studies on thiamine phosphates, (ii) physicochemical properties of s-benzoylthiamine o-monophosphate", the Vitamin Society of Japan, Takamine Laboratory, 1961, 9 pages.
Ito, "Synthesis, properties and application of sodium Acylthiosulfate (No. 4), Synthesis of SAcylthiamine Derivatives", Journal of the Pharmaceutical Society of Japan, 1962, vol. 82, No. 6, pp. 883-888.
Japanese Patent Application No. 2015-537105: Notification of Reasons for Refusal dated Jul. 19, 2016, 8 pages.
Kanaka, "Concise explanation of the relevance of Handbook of organic compound crystal production", Kodansha Co., Ltd., 2008, pp. 17-23, 37-40, 45-51, 57-65.
Kojima, "Study on High Efficiency Screening of Crystal in Drug R & D", Pharmaceutics, Sep. 1, 2008, vol. 68, No. 5, pp. 344-349.
Takada , "API form screening and selection in drug discovery stage", Pharm Stage, Jan. 15, 2007, vol. 6, No. 10, pp. 20-25.

* cited by examiner

CRYSTALLINE POLYMORPHS OF BENFOTIAMINE, PROCESS FOR PREPARATION AND ITS USE THEREOF

Matter enclosed in heavy brackets [ ] appears in the original patent but forms no part of this reissue specification; matter printed in italics indicates the additions made by reissue; a claim printed with strikethrough indicates that the claim was canceled, disclaimed, or held invalid by a prior post-patent action or proceeding.

FIELD OF THE INVENTION

The present invention is directed to crystalline polymorphs of benfotiamine, its methods of preparation and its pharmaceutical composition in preventing and treating vitamin B1 deficiency and metabolic disorders, mental illness and disorders, diabetes complications, neurodegenerative diseases. The present invention relates to the field of crystalline polymorphs of medical chemistry.

BACKGROUND OF THE INVENTION

Benfotiamine has previously been disclosed in patent US19623064000. Its full name is S-benzoylthiamine O-monophosphate, generic name is benfotiamine, chemical name is Benzenecarbothioic acid, chemical name of formula is S-[2-[[(4-amino-2-methyl-5 pyrimidinyl)methyl]formylamino]-1-[2- (phosphonooxy)ethyl]-1 -propenyl]ester, the formula is C19H23N4O6PS and molecular weight is 466.45. It has the following chemical structural:

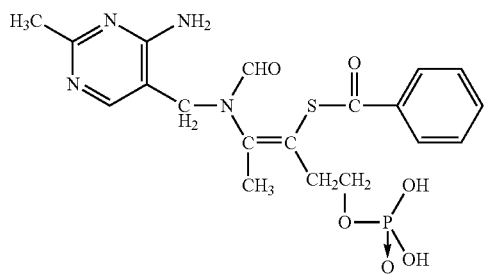

A substance with the same chemical composition may crystallize with two or more different spatial lattice arrangements. This phenomenon is called polymorphism. The polymorphic behavior of drugs can be of crucial importance in pharmacy and pharmacology, which takes tremendous impacts on drug quality. Varied crystalline forms may differ from each other with respect to one or more physical properties, such as crystal shape, melting point, hardness, solubility and dissociation, state stability and compaction behavior. The differences in physical properties exhibited by polymorphs affect pharmaceutical parameters such as storage stability, bioavailability and efficacy. Therefore, new drug R&D should give more attention to the research on drug polymorphism and crystalline control.

Benfotiamine is the fat-soluble derivative of vitamin B1, which greatly improve low-bioavailability of water-soluble vitamin B1, elevating thiamine level in blood and tissues, so as to its therapeutic efficacy. Indications for benfotiamine: (1) prevention and treatment of vitamin B1 deficiency; (2) additional supplement for vitamin B1 inadequacy from diet malabsorption (due to fatigue, hyperthyroidism, pregnancy, lactation, intensive physical labor); (3) wernicke's encephalopathy; (4) beriberi; (5) any other diseases result from vitamin B1 deficiency and disorders, such as neuropathy, muscle pains, joint pains, peripheral polyneuritis, peripheral nerve paralysis, myocardial metabolic disorder, constipation and other gastrointestinal dysfunction. Benfotiamine has been industrialized and distributed in America, Japan, Europe and other countries as vitamin B1 supplements.

Recent study demonstrates that benfotiamine also exhibits notable beneficial effect on diabetes peripheral neuropathy and retinopathy. Additionally, our study also illustrates that benfotiamine is useful in preventing and treating Alzheimer's disease (AD) and aging.

AD is an aging-related progressive neurodegenerative disease, of which the most common early symptoms are cognitive and behavior impairments. The incidence of AD increases dramatically with the ageing of the society. There were 6 million people in China with AD. AD is predicted to affect 30 million individuals globally by 2050. The death rates of cancers, stroke, and cardiovascular diseases as the leading cause of the death decrease according to the progress of medical therapy, but AD incidence is still roaring in large percentage. Additionally, due to long-lasting and high impairment rate of AD, it has turned into one of the most severe life-threatening diseases in $21^{st}$ century. The medical treatment costs of AD have been calculated to 604 billion US dollars in 2010, which account for almost 1% of global GDP.

As of nowadays, including China and America, two categories of drugs have been approved for AD treatment: acetylcholinesterase inhibitors and N-methyl-D-asparate receptor antagonist. However, no medication has been clearly shown to delay or halt the progression of the disease. Benfotiamine has been proved to reduce celebral β-amyloid (Aβ) deposition and tau hyperphosphorylation, subsequently alleviating the AD pathologic occurrence.

Benfotiamine is mainly administered by tablets and powders, but rarely disclosing the exact crystalline forms involved in these drugs. No systematic researches have been carried out in crystalline polymorphs of benfotiamine. The present invention is related to a systematic insight of crystalline polymorphs of benfotiamine. The characters of diverse crystalline forms of benfotiamine and their potential for new drug development are disclosed.

Three documents have been found to be the most closely related to the present invention on the basis of technical features:

D1: JP昭 37-13484B (Sankyo company, Ltd.)(Oct. 9, 1962), discloses a colorless needle-like purified benfotiamine crystal, with a melting point of about 160° C.-162° C.

D2: JP昭 37-16042B (Sankyo company Ltd.)(Aug. 10, 1962), discloses three benfotiamine crystalline forms, comprising crystalline form α (C19H23O6N4SP.2H2O, melting point about 165° C.), crystalline form β (C19H23O6N4SP.15H2O, melting point about 150° C.), and crystalline form δ (C19H23O6N4SP, melting point about 195° C.).

D3: 伊藤 憲等，ビタミン B1ン酸エステの研 第(報告) S-Benzoylthiamine O-Monophosphate 第の生成，高峰研 , 究所年報 , 1962年，の結晶形とそ 1巻，第 64-66頁 , ISSN: 0371-8670, discloses benfotiamine crystalline form δ and its hydrates.

D2 discloses a method for making benfotiamine crystalline form α by keeping temperature 0-5° C. and adjusting pH to 4, which is theoretically identical to the process of preparing benfotiamine crystalline form disclosed in example 1 of D1. We further confirm that benfotiamine crystalline form in D1 and benfotiamine crystalline form α in D2 are the same through their melting point. The hydrates crystalline forms of benfotiamine disclosed in D3 are equivalent to crystalline form α and γ in D2. D2 and D3 disclose a benfotiamine crystalline form δ without crystal water, of which the melting point is 195° C.

SUMMARY OF THE INVENTION

The present invention is directed to crystalline polymorphs of benfotiamine.

The present invention discloses a benfotiamine crystal, wherein the form can be any one of crystal forms below:

Crystalline form A, characterized by an X-ray powder diffraction pattern with significant peaks at diffraction angles (2θ) values) of about 11.317°, 16.377°, 17.874°, 18.543°, 19.313°, 20.850°, 21.295°, 24.858°, 25.142°.

Crystalline form B, characterized by an X-ray powder diffraction pattern with significant peaks at diffraction angles (2θvalues) of about 11.459°, 16.883°, 18.644°, 20.669°, 21.295°, 22.773°, 24.817°, 25.728°, 27.327°.

Crystalline form C, characterized by an X-ray powder diffraction pattern with significant peaks at diffraction angles (2θvalues) of about 10.811°, 11.338°, 14.516°, 16.984°, 18.684°, 19.352°, 20.809°, 21.336°, 22.854°.

Crystalline form D, characterized by an X-ray powder diffraction pattern with significant peaks at diffraction angles (2θvalues) of about 10.690°, 11.033°, 14.414°, 15.365°, 15.952°, 18.725°, 24.350°, 25.081°, 25.323°.

Crystalline form E, characterized by an X-ray powder diffraction pattern with significant peaks at diffraction angles (2θvalues) of about 9.334°, 11.863°, 12.633°, 13.260°, 13.484°, 14.395°, 15.588°, 17.206°, 18.015°, 18.948°, 19.635°, 21.276°, 22.025°, 23.703°, 24.352°, 24.938°, 26.314°, 27.023°.

In one embodiment, crystalline form A is characterized by an X-ray powder diffraction pattern with significant peaks at diffraction angles (2θvalues) of about 8.869°, 11.317°, 13.665°, 14.839°, 16.377°, 17.874°, 18.543°, 19.313°, 20.850°, 21.295°, 22.853°, 24.858°, 25.142°, 27.631°, 28.864°.

In a further embodiment, crystalline form A is fundamentally consistent with FIG. 1a in an X-ray powder diffraction pattern.

In a still further embodiment, crystalline form A is fundamentally consistent with FIG. 1b, 1c, 1d in differential scanning calorimetry (DSC), infrared spectroscopy (IR), raman spectroscopy respectively.

In one embodiment, crystalline form B is characterized by an X-ray powder diffraction pattern with significant peaks at diffraction angles (2θ values) of about 11.459°, 15.122°, 16.883°, 17.693°, 18.644°, 19.271°, 20.669°, 21.295°, 22.773°, 24.817°, 25.728°, 27.327°, 29.128°.

In a further embodiment, crystalline form B is fundamentally consistent with FIG. 2a in an X-ray powder diffraction pattern.

In a still further embodiment, crystalline form B is fundamentally consistent with FIG. 2b, 2c, 2d in differential scanning calorimetry (DSC), infrared spectroscopy (IR), raman spectroscopy respectively.

In one embodiment, crystalline form C is characterized by an X-ray powder diffraction pattern with significant peaks at diffraction angles (2θ values) of about 8.889°, 10.811°, 11.338°, 13.908°, 14.516°, 15.223°, 16.984°, 17.793°, 18.684°, 19.352°, 20.809°, 21.336°, 22.854°, 23.276°, 25.424°, 28.561°, 33.054°.

In a further embodiment, crystalline form C is fundamentally consistent with FIG. 3a in an X-ray powder diffraction pattern.

In a still further embodiment, crystalline form C is fundamentally consistent with FIG. 3b, 3c, 3d in differential scanning calorimetry (DSC), infrared spectroscopy (IR), raman spectroscopy respectively.

In one embodiment, crystalline form D is characterized by an X-ray powder diffraction pattern with significant peaks at diffraction angles (2θ values) of about 10.690°, 11.033°, 14.414°, 15.365°, 15.952°, 18.725°, 19.310°, 19.797°, 21.032°, 21.256°, 24.350°, 25.081°, 25.323°, 28.318°.

In a further embodiment, crystalline form D is fundamentally consistent with FIG. 4a in an X-ray powder diffraction pattern.

In a still further embodiment, crystalline form D is fundamentally consistent with FIG. 4b, 4c, 4d in differential scanning calorimetry (DSC), infrared spectroscopy (IR), raman spectroscopy respectively.

In one embodiment, crystalline form E is characterized by an X-ray powder diffraction pattern with significant peaks at diffraction angles (2θ values) of about 9.334°, 11.863°, 12.633°, 13.260°, 13.484°, 14.395°, 15.588°, 17.206°, 18.015°, 18.948°, 19.635°, 20.042°, 21.276°, 22.025°, 23.703°, 24.352°, 24.938°, 26.314°, 27.023°, 30.828°, 32.083°.

In a further embodiment, crystalline form E is fundamentally consistent with FIG. 5a in an X-ray powder diffraction pattern.

In a still further embodiment, crystalline form E is fundamentally consistent with FIG. 5b, 5c, 5d in differential scanning calorimetry (DSC), infrared spectroscopy (IR), raman spectroscopy respectively.

The present invention is directed to the process of preparing the crystalline of benfotiamine of the following methods:

Method 1: Crystalline form E of benfotiamine was suspended in an organic solvent, followed by stirring until complete dissolving. Then, the crystalline form A benfotiamine was obtained by evaporated slowly under 25° C.; or Method 2: Crystalline form E of benfotiamine was suspended in an organic solvent mixture of methanol and dichloromethane (volume ratio 1:3), followed by stirring until complete dissolving. Other poor organic solvent was then added slowly add while being stirred. Then, the crystalline form A was obtained by filtered and evaporated in the air; or Method 3: Crystalline form E of benfotiamine was suspended in an organic solvent, followed by stirring in a hybrid oven for at least 24 h. Then, the crystalline form B was obtained by filtered and evaporated in the air; or Method 4: Crystalline form E of benfotiamine was suspended in an organic solvent and the mixture was heated to 60° C. while being stirred until complete dissolving. After the addition was complete the mixture was cooled on ice bath while being stirred. Then, the crystalline form C was obtained by filtered and evaporated in the air; or Method 5: Crystalline form E of benfotiamine was suspended in an organic solvent, followed by stirring using a stirrer for at least 24 h. Then, the crystalline form D was obtained by filtered and evaporated in the air; or In one embodiment, the organic solvent includes at least one member selected from the group consisting of ketones, ethers, aliphatic hydrocarbons, aromatic hydrocarbons, esters, nitriles, alcohols, halogenated hydrocarbons, and mixtures thereof, which dissolves the benfotiamine and does not ruin its structure.

In a further embodiment, the organic solvent includes at least one member selected from the group consisting of methanol, ethanol, isopropanol, pentanol, acetone, 2-butanone, tetrahydrofuran, nitromethane, acetonitrile, chloroform, dichloromethane, methyl tert-butyl ether and mixtures thereof.

The present invention is directed to a pharmaceutical composition comprising a therapeutically effective amount of crystalline benfotiamine and at least any one form pharmaceutically acceptable excipients according to claims 1 to 16 which contain pharmaceutically effective doses.

In one embodiment, pharmaceutically acceptable excipients comprise at least one member selected from fillers, disintegrants, binders, lubricants and mixtures thereof.

In another embodiment, fillers comprise at least one member selected from starch, lactose, crystalline cellulose, dextrin, mannitol, oxidase, calcium sulfate and mixtures thereof.

In another embodiment, disintegrants comprise at least one member selected from carboxymethylcellulose and its salt, crosslinked carboxymethylcellulose and its salt, crosslinked polyvinylpyrrolidone, sodium carboxymethyl starch, low-substituted hydroxypropylcellulose and mixtures thereof.

In another embodiment, binders comprise at least one member selected from polyvinylpyrrolidone, hydroxypropyl methyl cellulose, starch slurry and mixtures thereof.

In another embodiment, lubricants comprise at least one member selected from magnesium stearate, calcium stearate and mixtures thereof.

The crystalline polymorphs of benfotiamine of the present invention are useful as they act directly on treatment of Vitamin B1 deficiency, metabolic disorders, mental illness and disorders, diabetes complications, neurodegerative diseases.

In one embodiment, neurodegerative diseases include Alzheimer's disease, vascular dementia and mental retard.

The present invention is a process for preparing and transforming diverse crystalline forms of benfotiamine through different synthesis routes and varied solvents and combinations. The crystalline polymorphs of the present invention are basically pure.

The present invention not only provides new crystalline forms of benfotiamine, but also provides its new solvates, especially hydrates.

The present invention discloses five benfotiamine crystalline forms, wherein crystalline form A is free of crystal water, crystalline form B contains one crystal water, crystalline form C is a solvate, crystalline form D has half of one crystal water, and crystalline form E has one crystal water. All the crystalline forms mentioned in the present invention are different from the crystalline form in D1 (特 37-13484B), crystalline forms α, γ in D2 (特 037-16042B) and the hydrates crystalline forms in D3(伊藤遣等). D2 and D3 disclose a benfotiamine crystalline form δ free of crystal water, of which the melting point is 195° C. The melting point of crystalline form A in present invention is 205° C., which is notably separate from crystalline form δ in accordance with common knowledge of skilled persons in this field by 10 degrees gap on melting point. Therefore, crystalline form A in present invention and crystalline form δ mentioned in D2 and D3 shall not be the same crystalline form.

BRIEF DESCRIPTION OF THE DRAWINGS

FIG. 6 is an overlapping pattern of FIG. 1a, 2a, 3a, 4a, and 5a.

DETAILED DESCRIPTION OF THE INVENTION

Figure 1A:
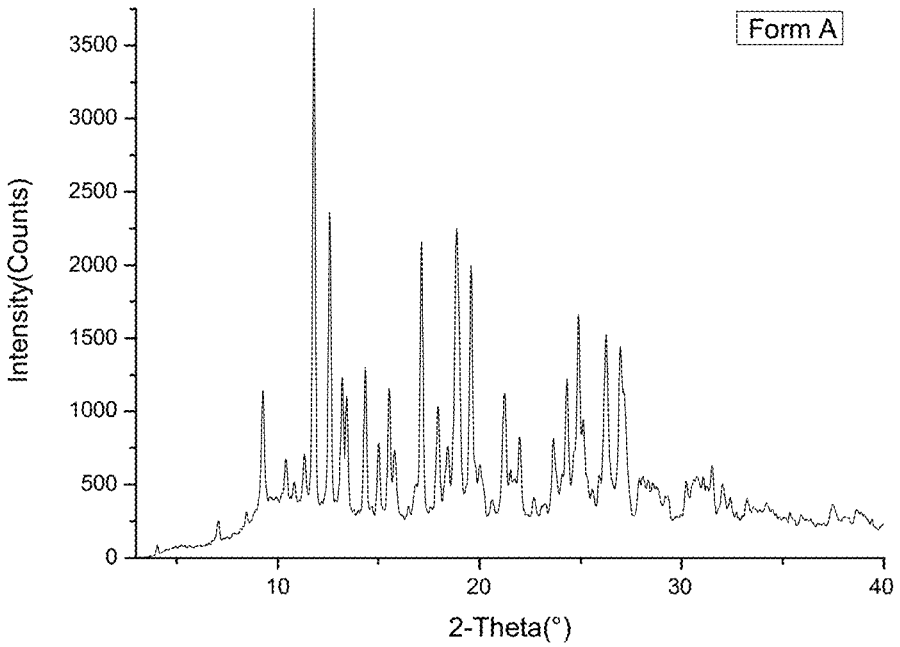
FIG. 1a is a characteristic X-ray Powder Diffraction (XRPD) pattern for crystalline form A of benfotiamine.

The foregoing and other objects, features and advantages of the invention will be apparent from the following more particular description of preferred embodiments of the invention, as illustrated in the accompanying drawings.

Laboratory Condition:

X-ray powder diffraction (XRPD) patterns of the polymorphs are measured on a Bruker D2 phaser X-ray powder diffractometer using Cu-Ka radiation at room temperature. The tube voltage and amperage ware set to 40 kV and 40 mA, respectively. A theta-two theta continuous scan at 0.1 sec/step from 3° to 40° 2θ is used.

In a further embodiment, the pattern of crystalline is characteristic in X-ray powder diffraction pattern. The band, especially in low angle, can be slightly changed in the relative intensity depending on crystallization condition, particle size, relative concentration of mixture and other measurement condition. Therefore, the relative intensity of diffraction angle 2θ of the crystalline form is not characteristic. The identification of crystalline form should be determined with the reference to the peak positions, but not their relative intensity. Additionally, the identification of crystalline form should not depend on one single peak, but comprehensive analysis of specific dI/II system. Moreover, during the identification of mixture, some deficiency of peak can occur due to decline in sample concentration. Therefore, it is not necessary to find safe bands appeared in highly pure samples. Even a single band may identify the crystalline form.

Differential Scanning calorimetry (DSC) thermograms of the polymorphs are measured on a DSC8500 (perkinelemer, USA). Analysis conditions were 10° C./min with a nitrogen purge.

Infrared spectroscopy (IR) pattern of the polymorphs are measured on a Nicolot-Magna FT-IR750 (Nicolot-Magna, USA) under room temperature, scanning at 4000-350 $cm^{-1}$.

Raman spectroscopy pattern of the polymorphs are measured on DXR (Thermo Scientific, USA) under room temperature, scanning at 3500-50 $cm^{-1}$.

Example 1: Preparation of Crystalline Form E of Benfotiamine

Step1: In a glass vial, 135 g of phosphoric acid (85%) was mixed with 155 g of phosphorus pentoxide, followed by stirring until complete dissolving. Then, 100 g of thiamine hydrochloride was added to the mixture, followed by stirring until no gas was observed. Hydrochloric acid was further added dropwise until no gas was observed.

Step2: The resultant mixture was added to acetone. Precipitated crystals were collected by filtration. The resultant thiamine monophosphate was dissolved in water, followed by adding 30% of sodium hydroxide to pH 12. Benzoyl chloride was then added slowly to the mixture, followed by stirring at room temperature for 3 hours. Precipitated crystals were collected by filtration.

Step3: Crystalline form E of benfotiamine was obtained by washing the precipitated crystals formed in step2 with ethanol.

The X-ray power diffraction pattern showed the compound was crystalline form E, as described below:

TABLE 1

Peak data list for crystalline form E of benfotiamine

| 2θ° | d/A | Intensity % |
|---|---|---|
| 8.545 | 10.3399 | 5.1 |
| 9.334 | 9.4673 | 25.2 |
| 10.465 | 8.4459 | 7.9 |
| 10.893 | 8.1155 | 4.6 |
| 11.863 | 7.4539 | 100 |
| 12.633 | 7.0011 | 53.2 |
| 13.26 | 6.6717 | 20.8 |
| 13.484 | 6.5613 | 22.4 |
| 14.395 | 6.1479 | 25.7 |
| 15.102 | 5.8615 | 6.8 |
| 15.588 | 5.6802 | 26.5 |
| 15.891 | 5.5722 | 11.9 |
| 17.206 | 5.1492 | 46.9 |
| 18.015 | 4.92 | 20.5 |
| 18.48 | 4.7971 | 5.5 |
| 18.948 | 4.6798 | 67.4 |
| 19.635 | 4.5175 | 52.2 |
| 20.042 | 4.4266 | 16.1 |
| 21.276 | 4.1727 | 30.8 |

TABLE 1-continued

Peak data list for crystalline form E of benfotiamine

| 2θ° | d/A | Intensity % |
|---|---|---|
| 21.618 | 4.1073 | 6.6 |
| 22.025 | 4.0324 | 24.6 |
| 23.703 | 3.7506 | 20.5 |
| 24.352 | 3.652 | 40.8 |
| 24.938 | 3.5676 | 71.2 |
| 26.314 | 3.3841 | 60 |
| 27.023 | 3.2968 | 48.5 |
| 27.954 | 3.1891 | 9.8 |
| 28.358 | 3.1446 | 7.5 |
| 28.805 | 3.0969 | 4.2 |
| 29.271 | 3.0486 | 7.1 |
| 30.828 | 2.898 | 14 |
| 31.132 | 2.8704 | 5.9 |
| 31.557 | 2.8327 | 8.7 |
| 32.083 | 2.7875 | 10.5 |
| 34.248 | 2.6161 | 4.9 |
| 35.971 | 2.4946 | 4.1 |
| 37.507 | 2.3959 | 3.9 |
| 38.703 | 2.3246 | 3.7 |
| 39.045 | 2.305 | 3.5 |

Figure 5A:
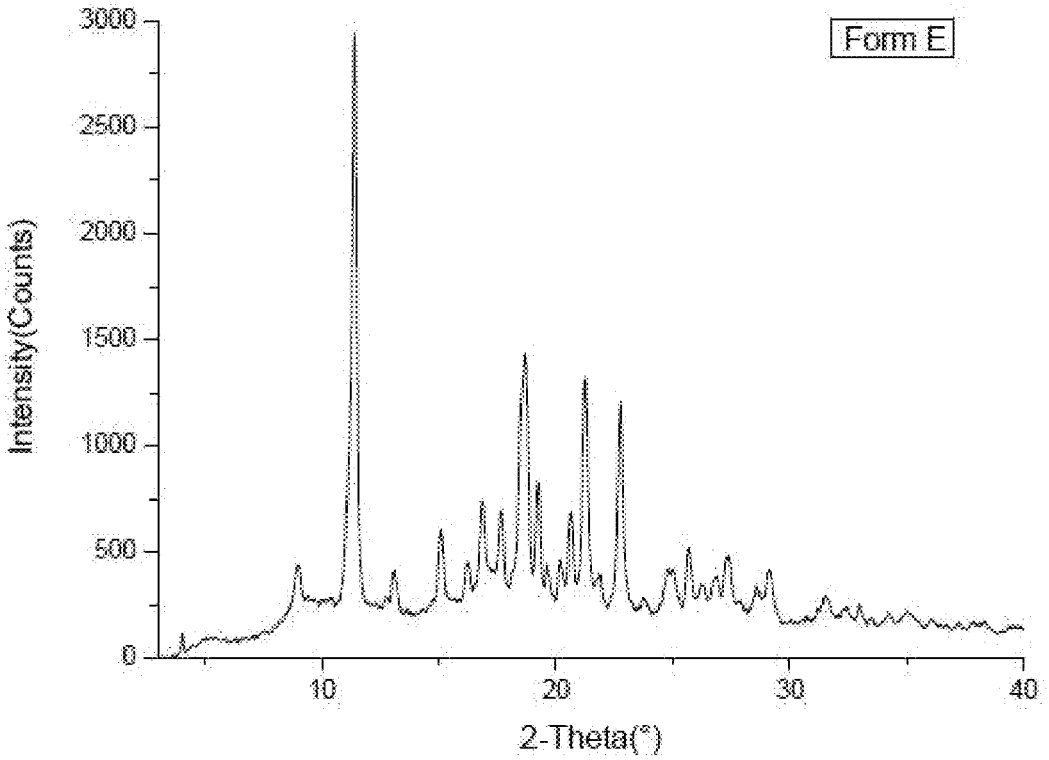
FIG. 5a is a characteristic X-ray Powder Diffraction (XRPD) pattern for crystalline form E of benfotiamine.
Figure 5B:
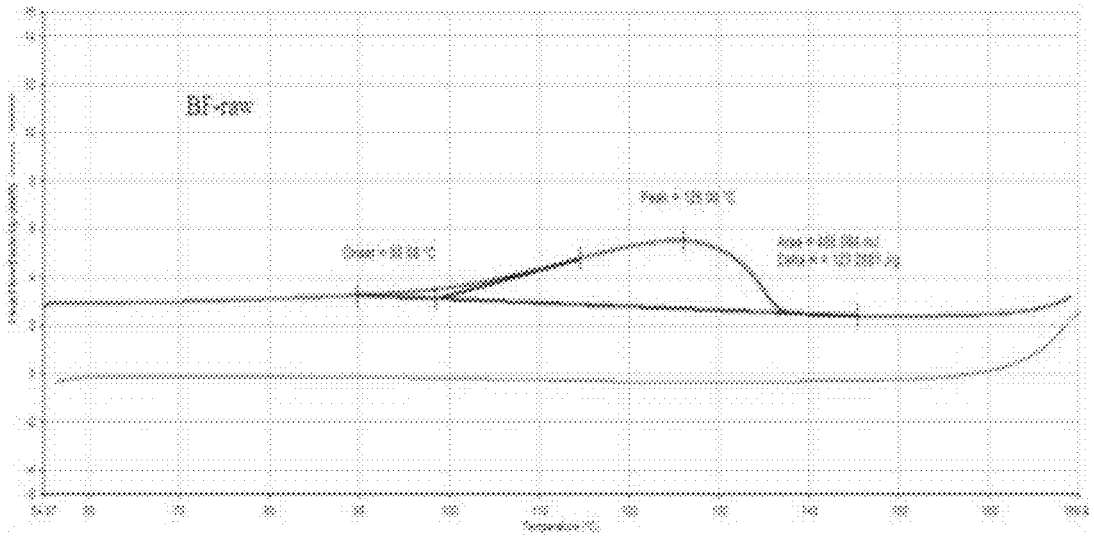
FIG. 5b is a characteristic Differential Scanning calorimetry (DSC) thermogram for crystalline form E of benfotiamine.
Figure 5C:
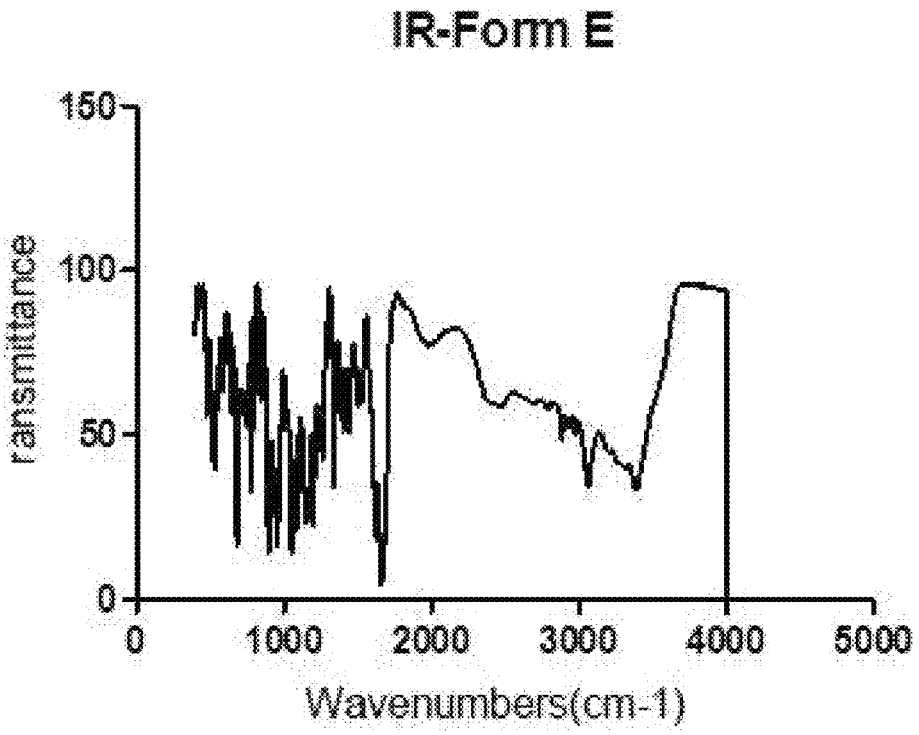
FIG. 5c is a characteristic infrared spectroscopy (IR) pattern for crystalline form E of benfotiamine.
Figure 5D:
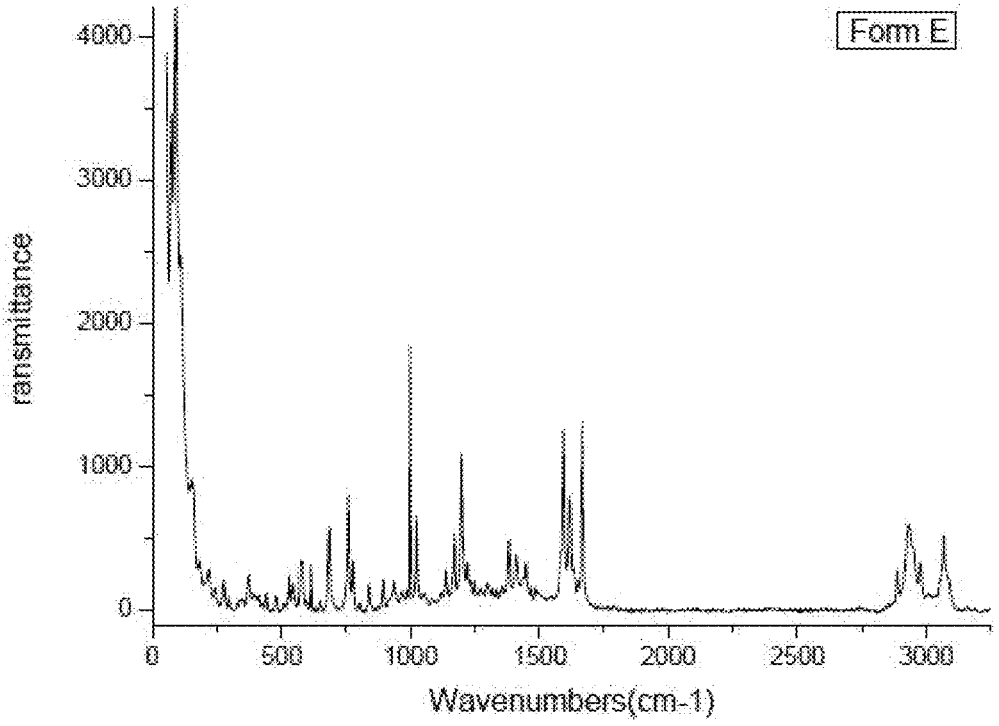
FIG. 5d is a characteristic raman spectroscopy pattern for crystalline form E of benfotiamine.
Figure 6:
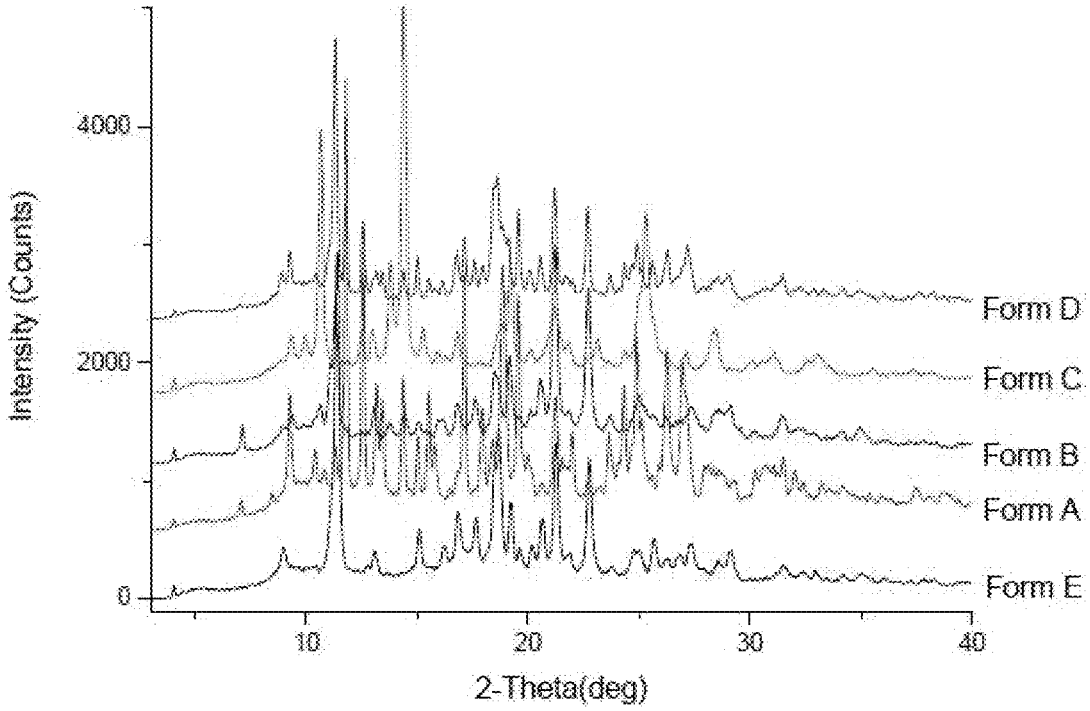
Figure 7:
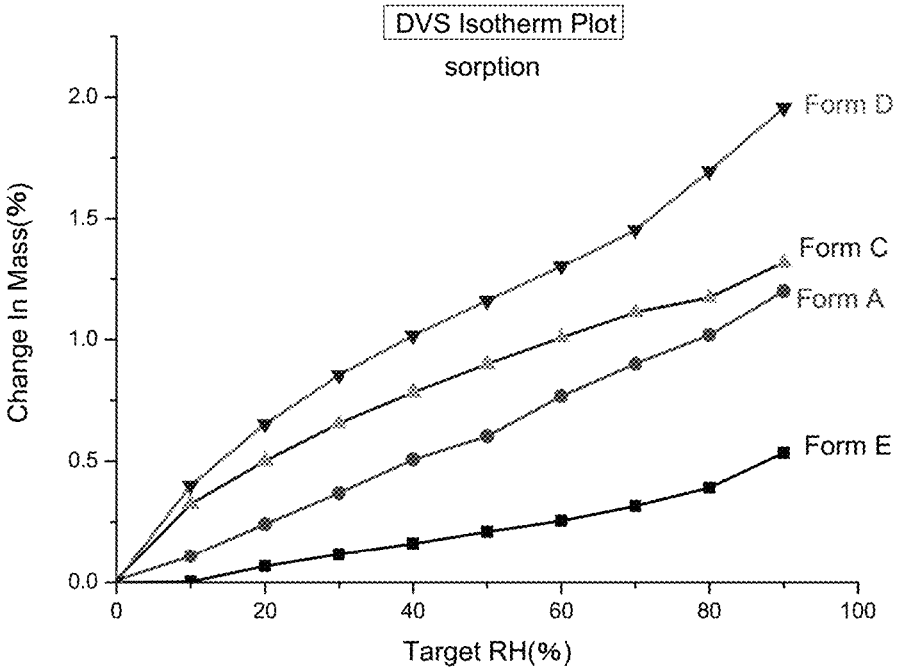
FIG. 7 is an overlapping pattern of FIG. 1b, 2b, 3b, 4b, and 5b.

The crystalline form E of benfotiamine was measured by differential scanning calorimetry (DSC), infrared spectroscopy (IR) and raman spectroscopy, respectively, as shown in FIG. 5b, 5c, 5d.

Example 2: Preparation of Crystalline Form A of Benfotiamine

In 200 μl of a mixture organic solvent of methanol and chloroform (volume ratio 1:2) was add 3 mg of the crystalline form E of benfotiamine, followed by stirring until complete dissolving. The crystals were collected by evaporating the resultant mixture slowly at 25° C. The X-ray power diffraction pattern showed the compound was crystalline form A, as described below:

TABLE 2

Peak data list for crystalline form A of benfotiamine

| 2θ/° | d/A | Intensity % |
|---|---|---|
| 8.869 | 9.9618 | 14.4 |
| 9.212 | 9.5917 | 3 |
| 10.852 | 8.1463 | 6.4 |
| 11.317 | 7.8123 | 100 |
| 12.409 | 7.1269 | 2.9 |
| 13.665 | 6.4745 | 11.5 |
| 14.17 | 6.245 | 4.1 |
| 14.839 | 5.9651 | 14.1 |
| 15.385 | 5.7544 | 4.7 |
| 15.711 | 5.6358 | 8 |
| 16.377 | 5.4082 | 19.4 |
| 17.086 | 5.1854 | 8.5 |
| 17.874 | 4.9585 | 22.9 |
| 18.543 | 4.7811 | 26.7 |
| 19.313 | 4.5922 | 34.3 |
| 19.822 | 4.4753 | 5.4 |
| 20.85 | 4.2569 | 26.6 |
| 21.295 | 4.1689 | 25.2 |
| 21.861 | 4.0622 | 4.9 |
| 22.853 | 3.8881 | 12.6 |
| 23.441 | 3.7918 | 9.4 |
| 24.067 | 3.6946 | 6.5 |
| 24.858 | 3.5788 | 26 |
| 25.142 | 3.5391 | 17 |
| 25.505 | 3.4895 | 4.3 |
| 25.871 | 3.4411 | 4.4 |

TABLE 2-continued

| Peak data list for crystalline form A of benfotiamine | | |
|---|---|---|
| 2θ/° | d/A | Intensity % |
| 26.517 | 3.3586 | 3.5 |
| 27.631 | 3.2257 | 10.3 |
| 27.913 | 3.1937 | 7.1 |
| 28.864 | 3.0906 | 10.3 |
| 29.39 | 3.0365 | 3.2 |
| 29.977 | 2.9783 | 3.9 |
| 30.543 | 2.9244 | 4.6 |
| 30.949 | 2.887 | 5.5 |
| 31.82 | 2.8099 | 2.9 |
| 32.77 | 2.7306 | 3.2 |
| 34.451 | 2.6011 | 4.9 |

Figure 1B:
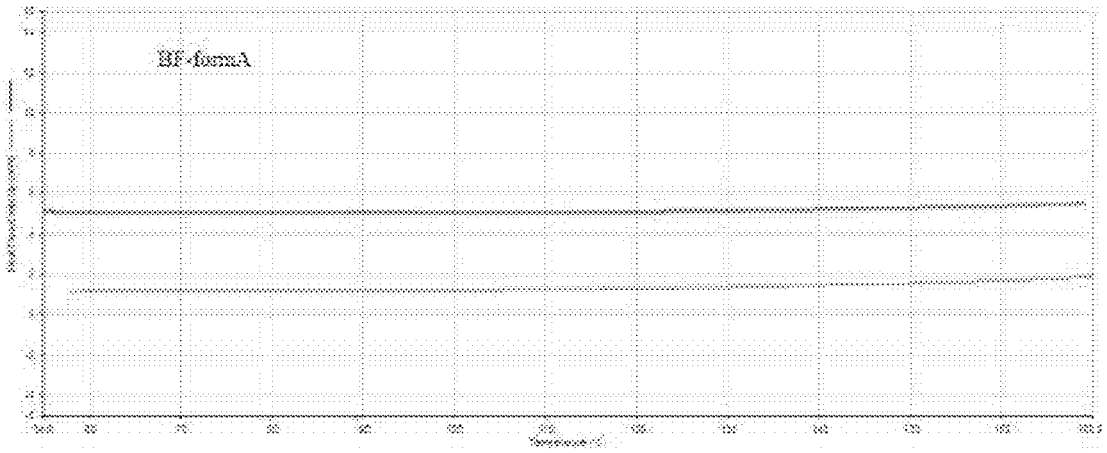
FIG. 1b is a characteristic Differential Scanning calorimetry (DSC) thermogram for crystalline form A of benfotiamine.
Figure 1C:
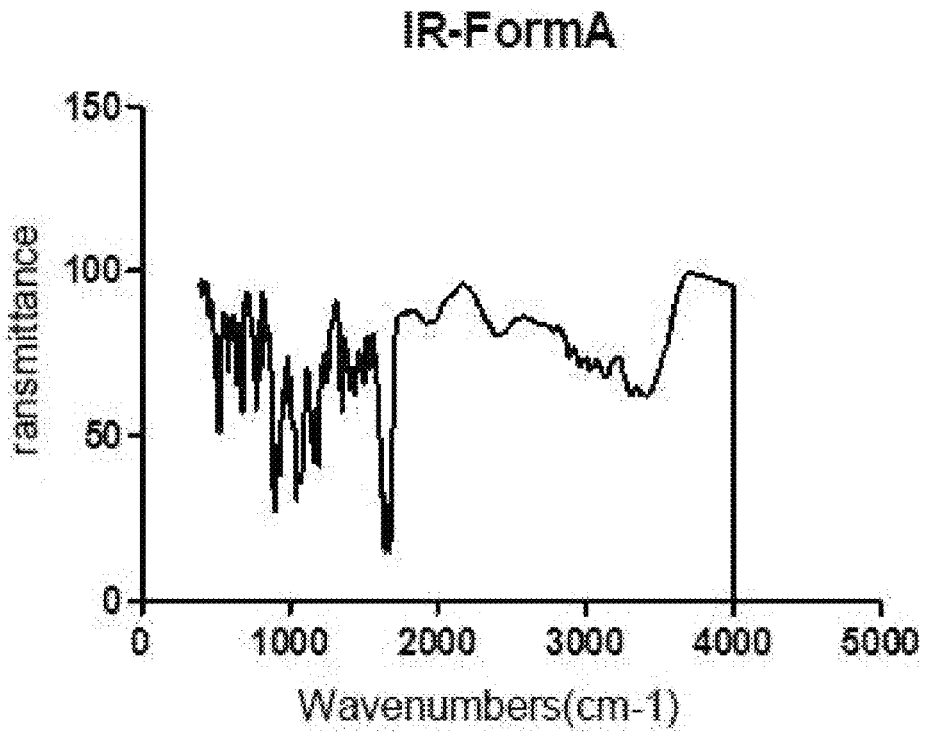
FIG. 1c is a characteristic infrared spectroscopy (IR) pattern for crystalline form A of benfotiamine.
Figure 1D:
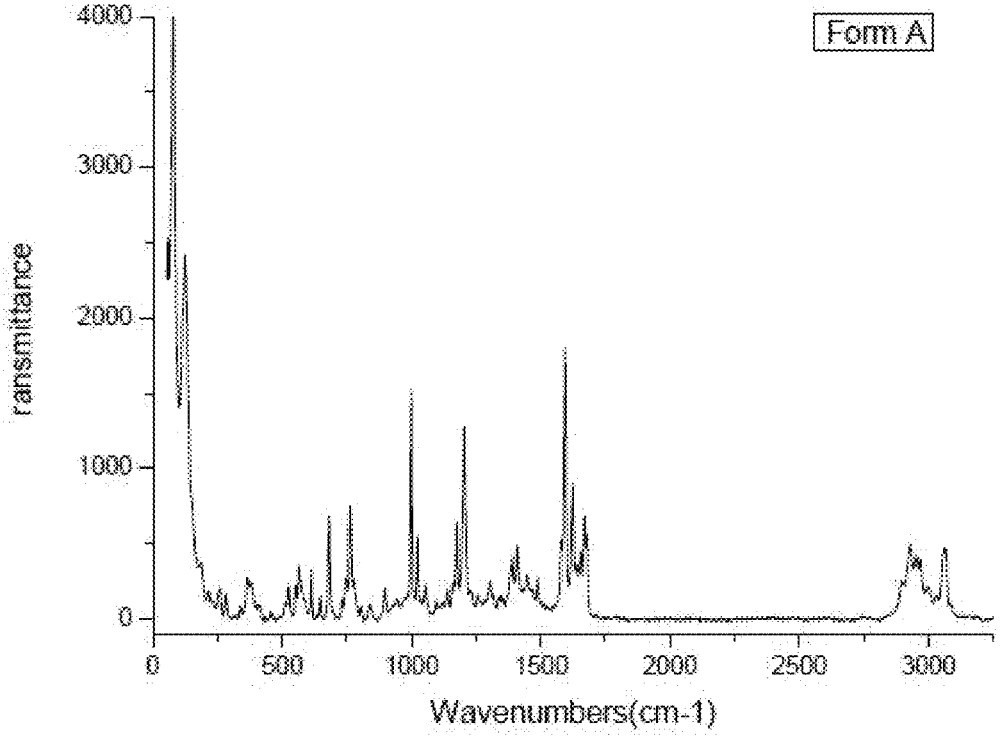
FIG. 1d is a characteristic raman spectroscopy pattern for crystalline form A of benfotiamine.

The crystalline form A of benfotiamine was measured by io differential scanning calorimetry (DSC), infrared spectroscopy (IR) and raman spectroscopy, respectively, as shown in FIG. 1b, 1c, 1d.

Example 3: Preparation of Crystalline Form A of Benfotiamine

In 200 μl of a mixture organic solvent of methanol and dichloromethane (volume ratio 1:3) was added 10 mg of the crystalline form E of benfotiamine (solubility 50 mg/ml). Then, 1 ml of the poor solvent of ethanol was slowly added to the mixture along device wall. Precipitated crystals were collected by filtration, followed by evaporated in the air. The X-ray power diffraction pattern showed the compound was crystalline form A, as described in table 2.

Example 4: Preparation of Crystalline Form A of Benfotiamine

Crystalline form A of benfotiamine was obtained in the same manner as in Example 3, except the poor solvent was isopropanol. The X-ray power diffraction pattern showed the compound was crystalline form A, as described in table 2.

Example 5: Preparation of Crystalline Form A of Benfotiamine

Crystalline form A of benfotiamine was obtained in the same manner as in Example 3, except the poor solvent was pentanol. The X-ray power diffraction pattern showed the compound was crystalline form A, as described in table 2.

Example 6: Preparation of Crystalline Form A of Benfotiamine

Crystalline form A of benfotiamine was obtained in the same manner as in Example 3, except the poor solvent was 2-butanone. The X-ray power diffraction pattern showed the compound was crystalline form A, as described in table 2.

Example 7: Preparation of Crystalline Form A of Benfotiamine

Crystalline form A of benfotiamine was obtained in the same manner as in Example 3, except the poor solvent was methylbenzene. The X-ray power diffraction pattern showed the compound was crystalline form A, as described in table 2.

Example 8: Preparation of Crystalline Form B of Benfotiamine 25 mg of crystalline form E of benfotiamine was suspended in 1 ml of methanol, followed by stirring for at least 24 h by a stirrer at 25° C. Then, the precipitated crystals were collected by filtration, followed by evaporated in the air for 10 min. The X-ray power diffraction pattern showed the compound was crystalline form B, as described in table 3.

TABLE 3

| Peak data list for crystalline form B of benfotiamine | | |
|---|---|---|
| 2θ/° | d/A | Intensity % |
| 9.05 | 9.7636 | 6.8 |
| 11.459 | 7.7157 | 100 |
| 13.139 | 6.7326 | 4.4 |
| 15.122 | 5.8539 | 9.6 |
| 16.276 | 5.4416 | 4.2 |
| 16.883 | 5.2472 | 14 |
| 17.693 | 5.0086 | 9.4 |
| 18.644 | 4.7553 | 55.6 |
| 19.271 | 4.6019 | 9.6 |
| 19.699 | 4.503 | 5.8 |
| 20.222 | 4.3877 | 5.3 |
| 20.669 | 4.2938 | 11.2 |
| 21.295 | 4.169 | 36 |
| 21.821 | 4.0696 | 5.9 |
| 22.773 | 3.9016 | 35.1 |
| 24.817 | 3.5848 | 11.2 |
| 25.728 | 3.4597 | 11.2 |
| 26.235 | 3.3941 | 5.7 |
| 26.841 | 3.3189 | 5 |
| 27.327 | 3.2609 | 12.3 |
| 28.662 | 3.1119 | 7 |
| 29.128 | 3.0632 | 11.5 |
| 31.577 | 2.831 | 5.9 |
| 32.326 | 2.7671 | 2.6 |
| 32.975 | 2.7141 | 4.5 |
| 34.169 | 2.622 | 2.4 |
| 34.937 | 2.5661 | 3.6 |
| 37.79 | 2.3786 | 2.7 |
| 38.417 | 2.3412 | 2.1 |

Figure 2A:
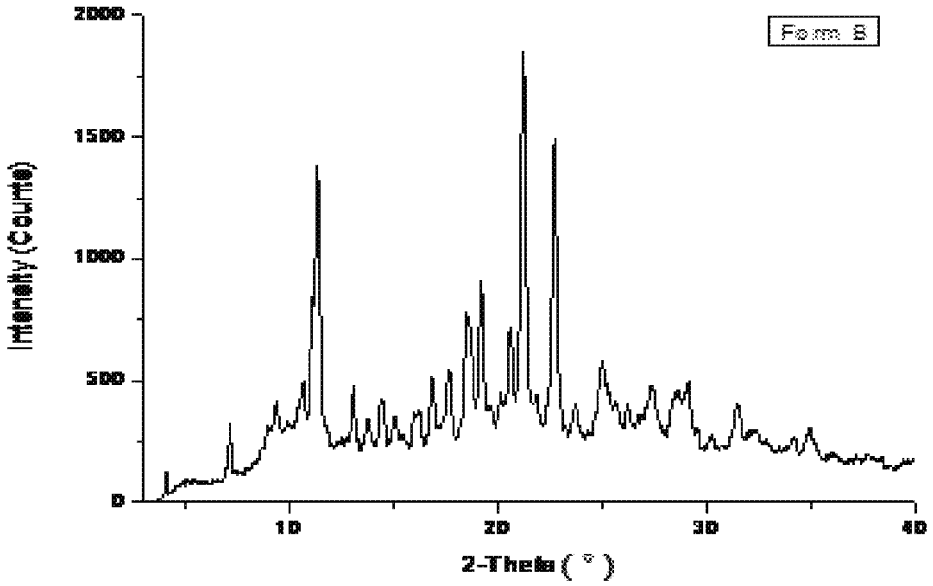
FIG. 2a is a characteristic X-ray Powder Diffraction (XRPD) pattern for crystalline form B of benfotiamine.
Figure 2B:
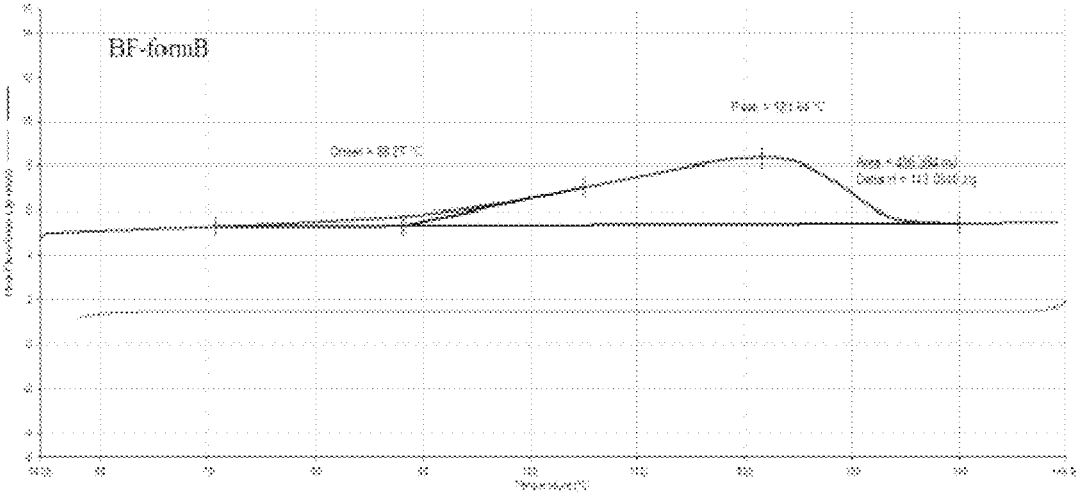
FIG. 2b is a characteristic Differential Scanning calorimetry (DSC) thermogram for crystalline form B of benfotiamine.
Figure 2C:
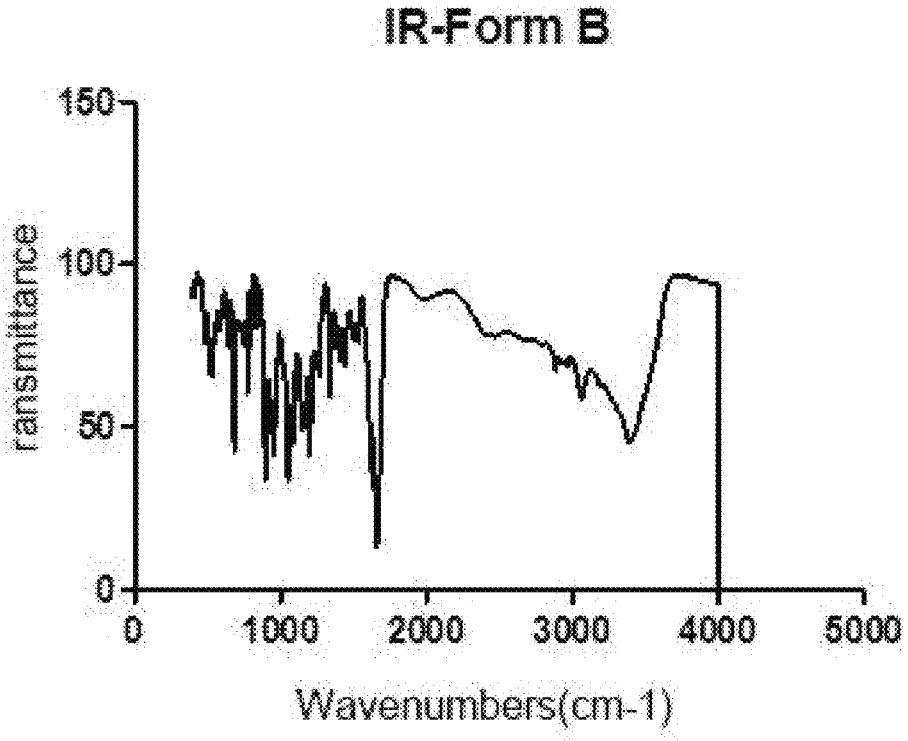
FIG. 2c is a characteristic infrared spectroscopy (IR) pattern for crystalline form B of benfotiamine.
Figure 2D:
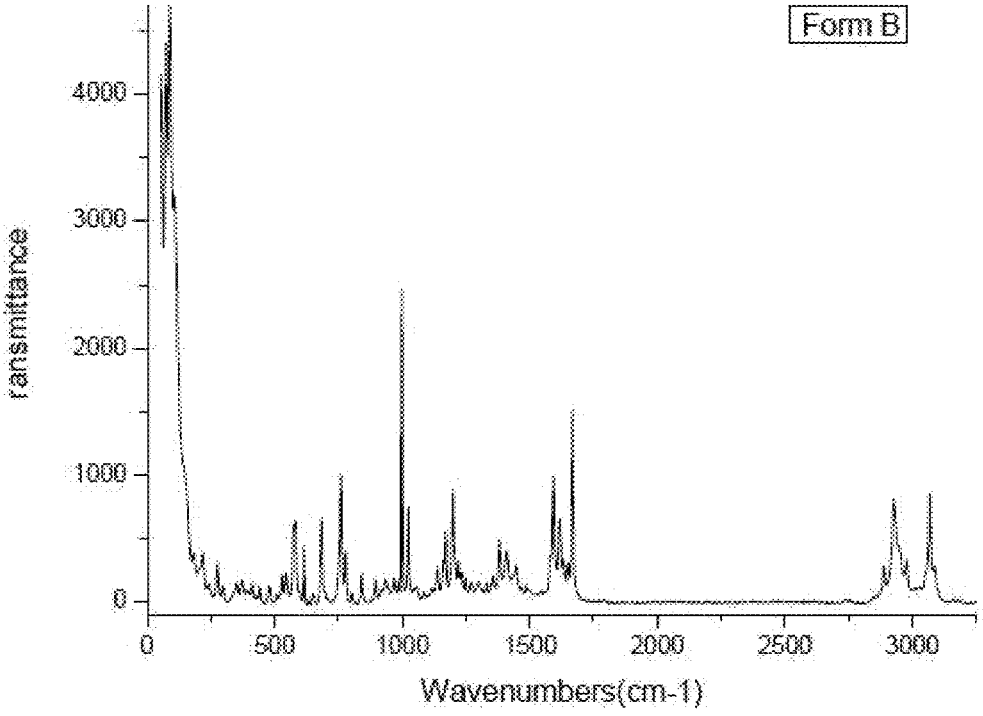
FIG. 2d is a characteristic raman spectroscopy pattern for crystalline form B of benfotiamine.

The crystalline form B of benfotiamine was measured by differential scanning calorimetry (DSC), infrared spectroscopy (IR) and raman spectroscopy, respectively, as shown in FIG. 2b, 2c, 2d.

Example 9: Preparation of Crystalline Form B of Benfotiamine

Crystalline form B of benfotiamine was obtained in the same manner as in Example 8, except the organic solvent was isopropanol. The X-ray power diffraction pattern showed the compound was crystalline form B, as described in table 3.

Example 10: Preparation of Crystalline Form C of Benfotiamine

In 0.5 ml of mixed solution of methanol and dichloromethane (volume ratio 1:1) was added 5 mg of crystalline form E of benfotiamine powder, followed by heating to 60° C. while being stirred until complete dissolving. Then, the resultant mixture was incubated on the ice bath, followed by stirring for 4 h. The resultant mixture may be stored at 4° C. overnight, if there is no precipitate appeared. And then, the precipitated crystals were collected by filtration, followed by evaporated. The X-ray power diffraction pattern showed the compound was crystalline form C, as described in table 4.

TABLE 4

| Peak data list for crystalline form C of benfotiamine | | |
|---|---|---|
| 2θ/° | d/A | Intensity % |
| 8.889 | 9.9404 | 15.2 |
| 9.496 | 9.3063 | 8.2 |
| 10.811 | 8.1766 | 62.1 |
| 11.338 | 7.7981 | 84.5 |
| 12.692 | 6.9686 | 8.8 |
| 13.179 | 6.7123 | 8.5 |
| 13.908 | 6.3623 | 17.6 |
| 14.516 | 6.0971 | 100 |
| 15.223 | 5.8155 | 13.2 |
| 16.984 | 5.2162 | 28.2 |
| 17.793 | 4.9809 | 15 |
| 18.684 | 4.7452 | 37.3 |
| 19.352 | 4.5829 | 67.4 |
| 20.809 | 4.2652 | 26.4 |
| 21.336 | 4.161 | 62.8 |
| 22.854 | 3.888 | 35.7 |
| 23.276 | 3.8184 | 11.3 |
| 25.424 | 3.5005 | 72.5 |
| 27.327 | 3.2608 | 7.7 |
| 28.561 | 3.1227 | 30.4 |
| 31.152 | 2.8686 | 7.8 |
| 33.054 | 2.7078 | 10.8 |

Figure 3A:
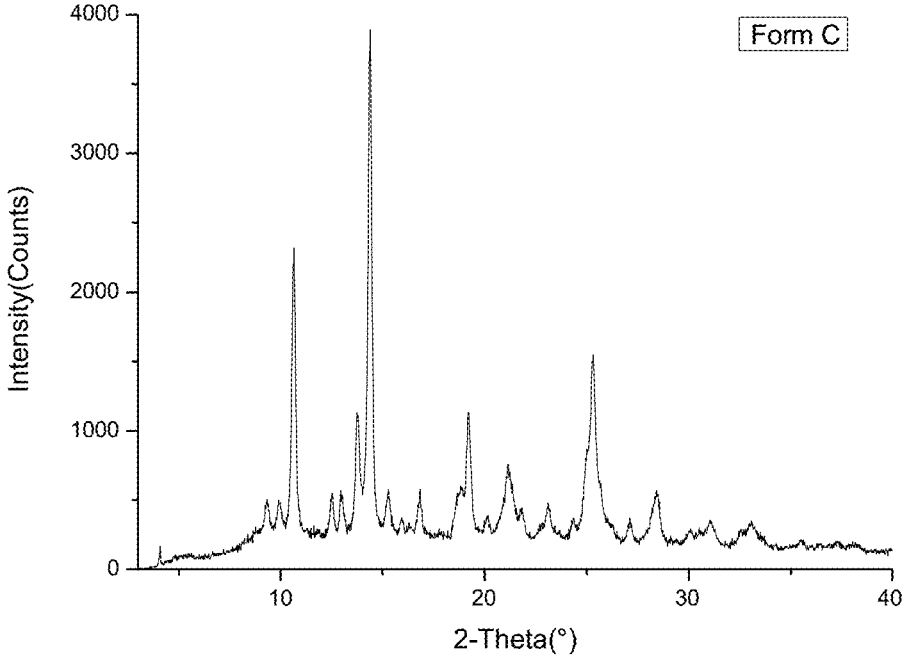
FIG. 3a is a characteristic X-ray Powder Diffraction (XRPD) pattern for crystalline form C of benfotiamine.
Figure 3B:
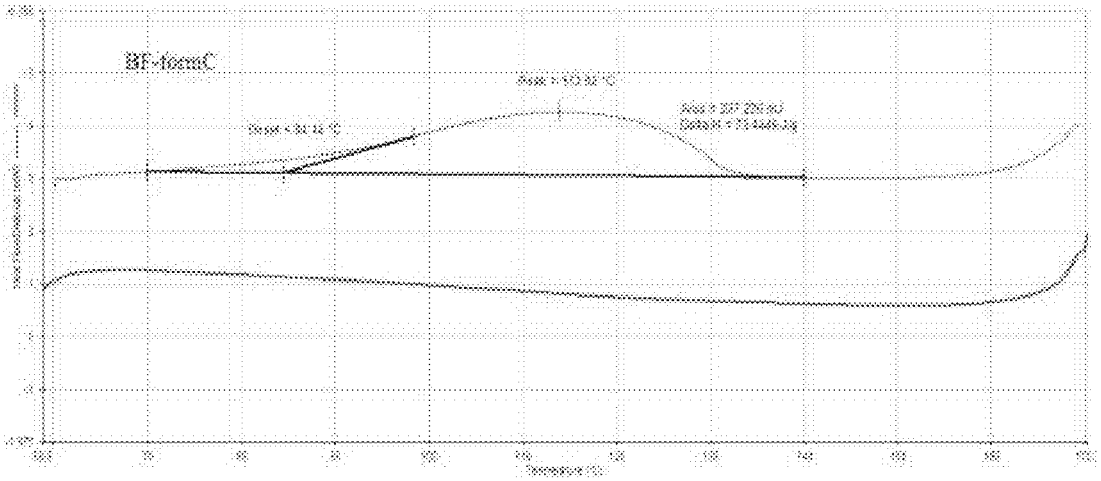
FIG. 3b is a characteristic Differential Scanning calorimetry (DSC) thermogram for crystalline form C of benfotiamine.
Figure 3C:
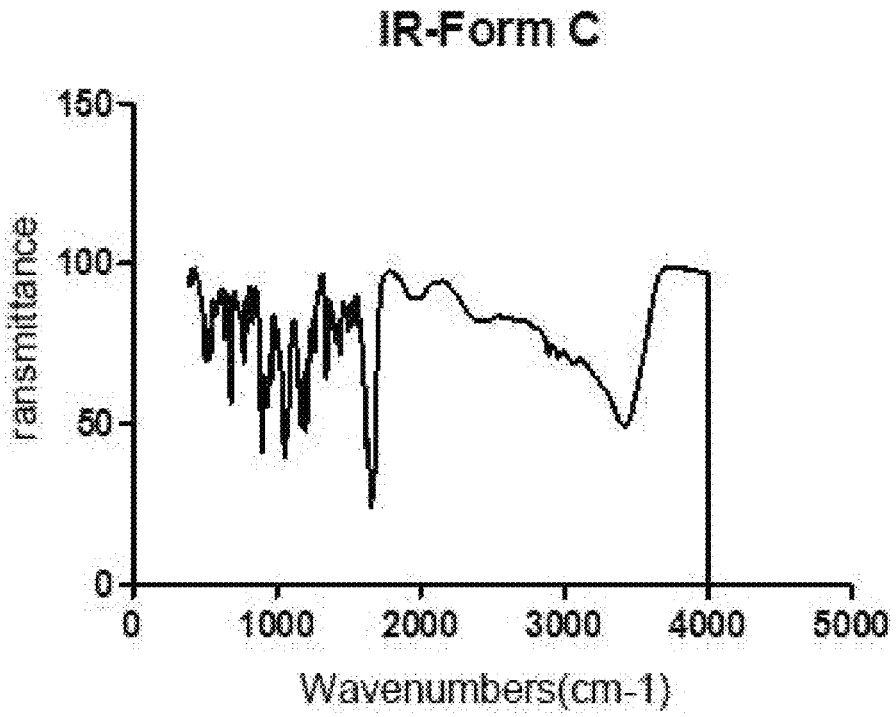
FIG. 3c is a characteristic infrared spectroscopy (IR) pattern for crystalline form C of benfotiamine.
Figure 3D:
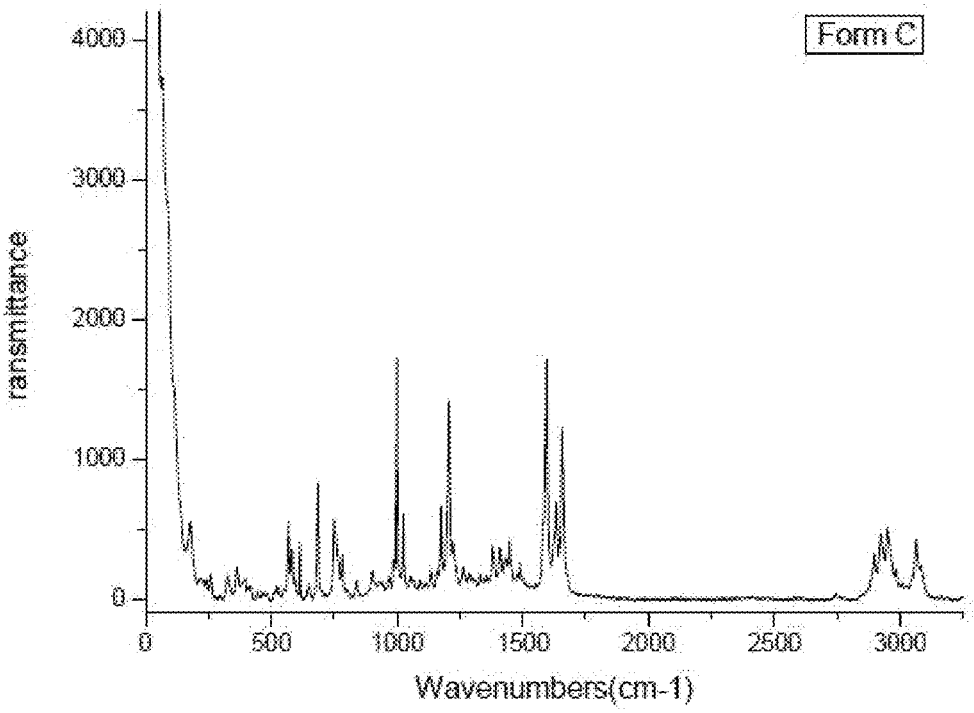
FIG. 3d is a characteristic raman spectroscopy pattern for crystalline form C of benfotiamine.

The crystalline form C of benfotiamine was measured by differential scanning calorimetry (DSC), infrared spectroscopy (IR) and raman spectroscopy, respectively, as shown in FIG. 3b, 3c, 3d.

Example 11: Preparation of Crystalline Form C of Benfotiamine

Crystalline form C of benfotiamine was obtained in the same manner as in Example 10, except the organic solvent was a mixture of methanol and dichloromethane (volume ratio 1:2). The X-ray power diffraction pattern showed the compound was crystalline form C, as described in table 4.

Example 12: Preparation of Crystalline Form C of Benfotiamine

Crystalline form C of benfotiamine was obtained in the same manner as in Example 10, except the organic solvent was a mixture of methanol and chloroform (volume ratio 1:2). The X-ray power diffraction pattern showed the compound was crystalline form C, as described in table 4.

Example 13: Preparation of Crystalline Form D of Benfotiamine

In 1 ml of ethanol was added 25 mg of crystalline form E of benfotiamine, followed by stirring at 25° C. by a stirrer for at least 24 h. The precipitated crystals were collected by filtration, followed by evaporated in the air for 10 min. The X-ray power diffraction pattern showed the compound was crystalline form D, as described in table 5.

TABLE 5

| Peak data list for crystalline form D of benfotiamine | | |
|---|---|---|
| 2θ/° | d/A | Intensity % |
| 6.843 | 12.9057 | 2.7 |
| 9.032 | 9.7828 | 4.3 |
| 9.353 | 9.448 | 3.7 |

TABLE 5-continued

| Peak data list for crystalline form D of benfotiamine | | |
|---|---|---|
| 2θ/° | d/A | Intensity % |
| 10.69 | 8.2692 | 29.6 |
| 11.033 | 8.0124 | 100 |
| 11.743 | 7.53 | 6.8 |
| 12.431 | 7.1145 | 5.2 |
| 13.766 | 6.4273 | 7.7 |
| 14.414 | 6.1399 | 31.6 |
| 15.365 | 5.7619 | 22.8 |
| 15.952 | 5.5511 | 21.2 |
| 16.924 | 5.2345 | 5.8 |
| 17.308 | 5.1192 | 9.5 |
| 18.118 | 4.8922 | 5.7 |
| 18.725 | 4.7349 | 21.5 |
| 19.31 | 4.5927 | 12.4 |
| 19.797 | 4.4809 | 13 |
| 21.032 | 4.2205 | 14.3 |
| 21.256 | 4.1765 | 13.6 |
| 22.896 | 3.881 | 9.9 |
| 24.35 | 3.6523 | 30.6 |
| 25.081 | 3.5476 | 15.5 |
| 25.323 | 3.5142 | 26.5 |
| 27.044 | 3.2943 | 6.3 |
| 28.318 | 3.1489 | 14.5 |
| 30.606 | 2.9185 | 4.5 |

Figure 4A:
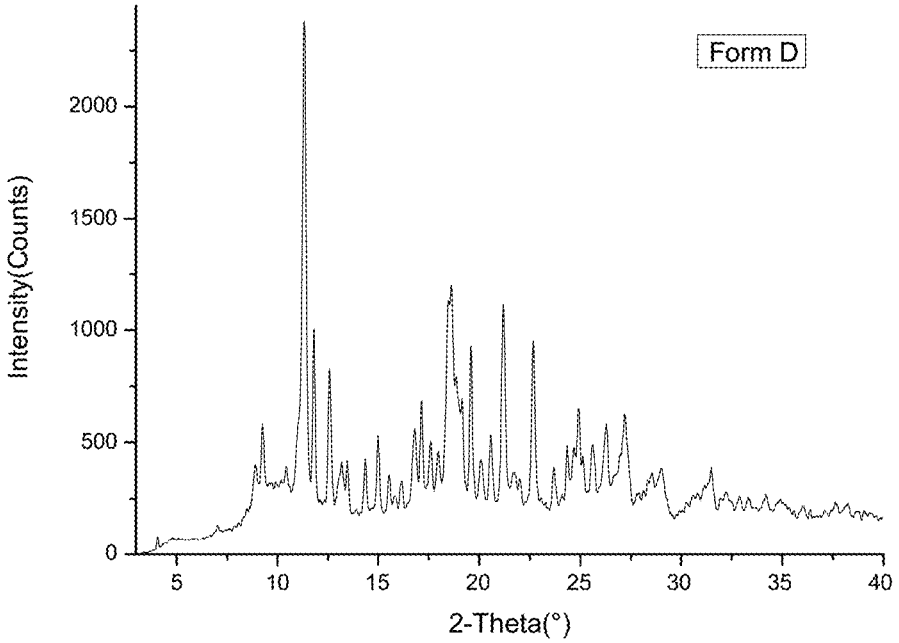
FIG. 4a is a characteristic X-ray Powder Diffraction (XRPD) pattern for crystalline form D of benfotiamine.
Figure 4B:
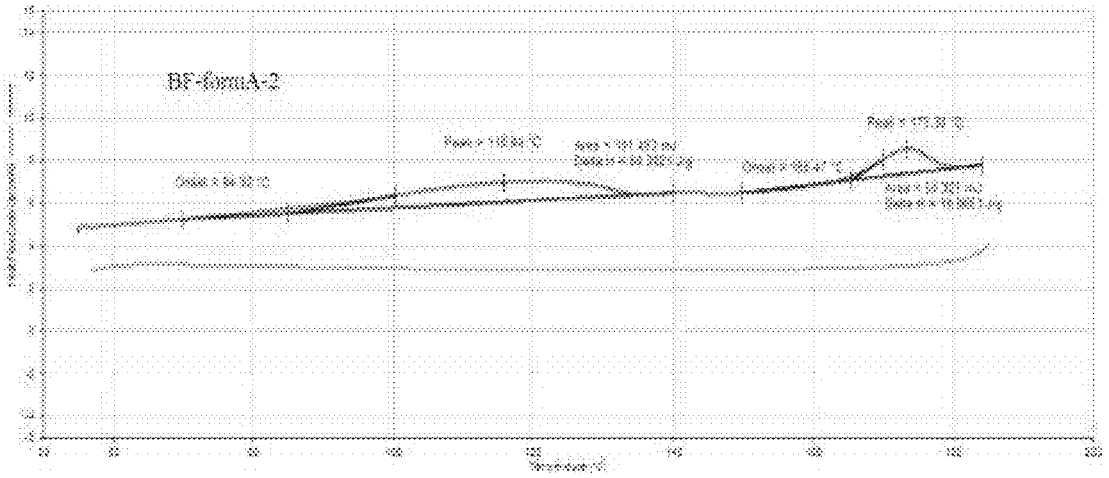
FIG. 4b is a characteristic Differential Scanning calorimetry (DSC) thermogram for crystalline form D of benfotiamine.
Figure 4C:
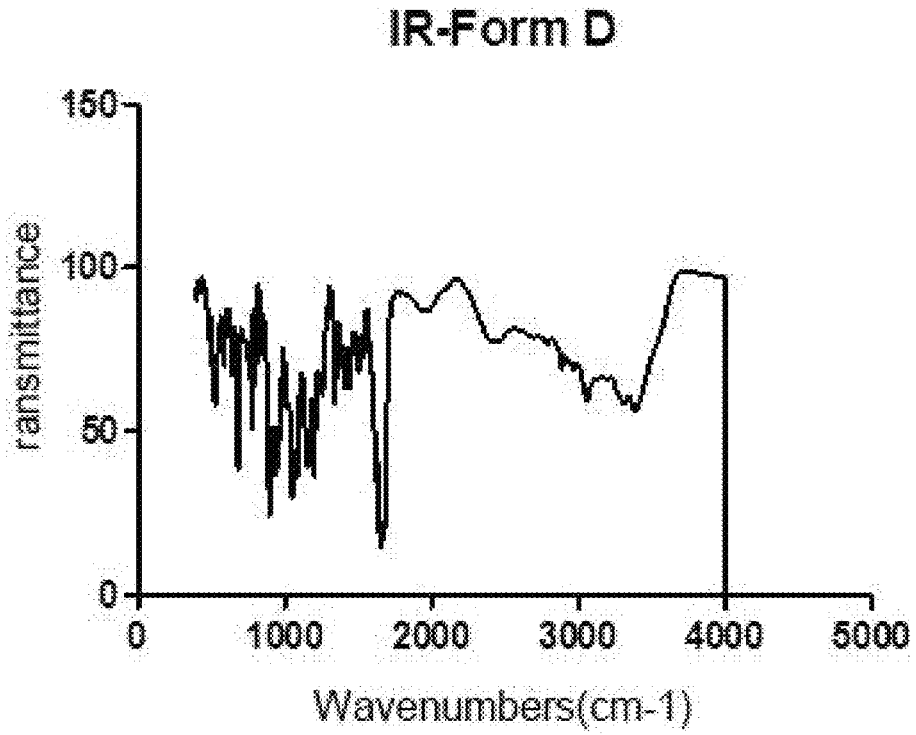
FIG. 4c is a characteristic infrared spectroscopy (IR) pattern for crystalline form D of benfotiamine.
Figure 4D:
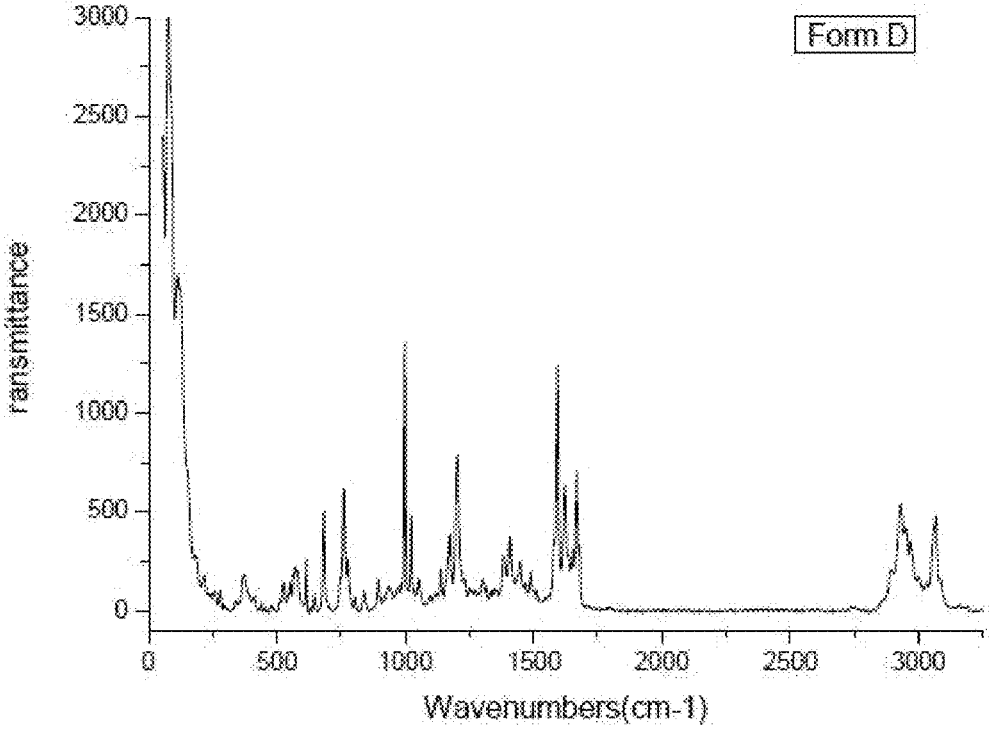
FIG. 4d is a characteristic raman spectroscopy pattern for crystalline form D of benfotiamine.

The crystalline form D of benfotiamine was measured by differential scanning calorimetry (DSC), infrared spectroscopy (IR) and raman spectroscopy, respectively, as shown in FIG. 4b, 4c, 4d.

Example 14: Preparation of Crystalline Form D of Benfotiamine

Crystalline form D of benfotiamine was obtained in the same manner as in Example 13, except the organic solvent was pentanol. The X-ray power diffraction pattern showed the compound was crystalline form D, as described in table 5.

Example 15: Preparation of Crystalline Form D of Benfotiamine

Crystalline form D of benfotiamine was obtained in the same manner as in Example 13, except the organic solvent was acetone. The X-ray power diffraction pattern showed the compound was crystalline form D, as described in table 5.

Example 16: Preparation of Crystalline Form D of Benfotiamine

Crystalline form D of benfotiamine was obtained in the same manner as in Example 13, except the organic solvent was 2-butanone. The X-ray power diffraction pattern showed the compound was crystalline form D, as described in table 5.

Example 17: Preparation of Crystalline Form D of Benfotiamine

Crystalline form D of benfotiamine was obtained in the same manner as in Example 13, except the organic solvent was tetrahydrofuran. The X-ray power diffraction pattern showed the compound was crystalline form D, as described in table 5.

Example 18: Preparation of Crystalline Form D of Benfotiamine

Crystalline form D of benfotiamine was obtained in the same manner as in Example 13, except the organic solvent was nitromethane. The X-ray power diffraction pattern showed the compound was crystalline form D, as described in table 5.

Example 19: Hygroscopicity Comparisons Among Four Crystalline Forms of Benfotiamine Dynamic vapor sorption analysis was used for measurement of the hygroscopicity of crystalline form A, C, D, and E under the scope of relative humidity (RH) from 5% to 95%. It indicated that hygroscopicity of the four crystalline forms was all under 2.0%, wherein the crystalline form E has the lowest hygroscopicity, and the crystalline form D has the highest hygroscopicity.

As used herein "basically pure" is that the crystals of the present invention preferably contains 90% or more of a crystalline substance, more preferably 95% or more, further preferably 96% or more, more further preferably 97% or more, especially preferably 98% or more, most preferably 99% or more of a crystalline substance, which used in X-ray powder diffraction (XRPD), raman spectroscopy, infrared spectroscopy (IR).

What is claimed is:

1. A benfotiamine crystal, wherein the form can be any one of the crystalline forms below:

Crystalline form A, characterized by an X-ray powder diffraction pattern with significant peaks at diffraction angles (20 values) of about 11.317°, 16.377°, 17.874°, 18.543°, 19.313°, 20.850°, 21.295°, 24.858°, 25.142°;

Crystalline form B, characterized by an X-ray powder diffraction pattern with significant peaks at diffraction angles (20 values) of about 11.459°, 16.883°, 18.644°, 20.669°, 21.295°, 22.773°, 24.817°, 25.728°, 27.327°;

Crystalline form C, characterized by an X-ray powder diffraction pattern with significant peaks at diffraction angles (20 values) of about 10.811°, 11.338°, 14.516°, 16.984°, 18.684°, 19.352°, 20.809°, 21.336°, 22.854°;

Crystalline form D, characterized by an X-ray powder diffraction pattern with significant peaks at diffraction angles (20 values) of about 10.690°, 11.033°, 14.414°, 15.365°, 15.952°, 18.725°, 24.350°, 25.081°, 25.323°; or Crystalline form E, characterized by an X-ray powder diffraction pattern with significant peaks at diffraction angles (20 values) of about 9.334°, 11.863°, 12.633°, 13.260°, 13.484°, 14.395°, 15.588°, 17.206°, 18.015°, 18.948°, 19.635°, 21.276°, 22.025°, 23.703°, 24.352°, 24.938°, 26.314°, 27.023°.

2. The crystalline compound of claim 1, wherein the crystalline form A is further characterized by an X-ray powder diffraction pattern with significant peaks at diffraction angles (20 values) of about 8.869°, 11.317°, 13.665°, 14.839°, 16.377°, 17.874°, 18.543°, 19.313°, 20.850°, 21.295°, 22.853°, 24.858°, 25.142°, 27.631°, 28.864°.

3. The crystalline compound of claim 1, wherein the crystalline form B is further characterized by an X-ray powder diffraction pattern with significant peaks at diffraction angles (20 values) of about 11.459°, 15.122°, 16.883°, 17.693°, 18.644°, 19.271°, 20.669°, 21.295°, 22.773°, 24.817°, 25.728°, 27.327°, 29.128°.

4. The crystalline compound of claim 1, wherein the crystalline form C is further characterized by an X-ray powder diffraction pattern with significant peaks at diffraction angles (20 values) of about 8.889°, 10.811°, 11.338°, 13.908°, 14.516°, 15.223°, 16.984°, 17.793°, 18.684°, 19.352°, 20.809°, 21.336°, 22.854°, 23.276°, 25.424°, 28.561°, 33.054°.

5. The crystalline compound of claim 1, wherein the crystalline form D is further characterized by an X-ray powder diffraction pattern with significant peaks at diffraction angles (20 values) of about 10.690°, 11.033°, 14.414°, 15.365°, 15.952°, 18.725°, 19.310°, 19.797°, 21.032°, 21.256°, 24.350°, 25.081°, 25.323°, 28.318°.

6. The crystalline compound of claim 1, wherein the crystalline form E is further characterized by an X-ray powder diffraction pattern with significant peaks at diffraction angles (20 values) of about 9.334°, 11.863°, 12.633°, 13.260°, 13.484°, 14.395°, 15.588°, 17.206°, 18.015°, 18.948°, 19.635°, 20.042°, 21.276°, 22.025°, 23.703°, 24.352°, 24.938°, 26.314°, 27.023°, 30.828°, 32.083°.

7. The crystalline compound of claim 2, wherein the crystalline form A is fundamentally consistent with FIG. 1a in X-ray powder diffraction pattern.

8. The crystalline compound of claim 3, wherein the crystalline form B is fundamentally consistent with FIG. 2a in X-ray powder diffraction pattern.

9. The crystalline compound of claim 4, wherein the crystalline form C is fundamentally consistent with FIG. 3a in X-ray powder diffraction pattern.

10. The crystalline compound of claim 5, wherein the crystalline form D is fundamentally consistent with FIG. 4a in X-ray powder diffraction pattern.

11. The crystalline compound of claim 6, wherein the crystalline form E is fundamentally consistent with FIG. 5a in X-ray powder diffraction pattern.

12. The crystalline compound of claim 2, wherein the crystalline form A is fundamentally consistent with FIG. 1b, 1c, 1d in differential scanning calorimetry (DSC), infrared spectroscopy (IR), and raman spectroscopy, respectively.

13. The crystalline compound of claim 3, wherein the crystalline form B is fundamentally consistent with FIG. 2b, 2c, 2d in differential scanning calorimetry (DSC), infrared spectroscopy (IR), and raman spectroscopy, respectively.

14. The crystalline compound of claim 4, wherein the crystalline form C is fundamentally consistent with FIG. 3b, 3c, 3d in differential scanning calorimetry (DSC), infrared spectroscopy (IR), and raman spectroscopy, respectively.

15. The crystalline compound of claim 5, wherein the crystalline form D is fundamentally consistent with FIG. 4b, 4c, 4d in differential scanning calorimetry (DSC), infrared spectroscopy (IR), and raman spectroscopy, respectively.

16. The crystalline compound of claim 6, wherein the crystalline form E is fundamentally consistent with FIG. 5b, 5c, 5d in differential scanning calorimetry (DSC), infrared spectroscopy (IR), and raman spectroscopy, respectively.

17. The process of preparing the crystalline compound of claim 1 comprising the methods of:

Method 1: Crystalline form E of benfotiamine [was] *is* suspended in an organic solvent, followed by stirring until complete dissolving, and the crystalline form A then [was] *is* obtained by evaporated slowly under 25° C.; or Method 2: Crystalline form E of benfotiamine [was] *is* suspended in an organic solvent mixture of methanol and dichloromethane (volume ratio 1:3), followed by stirring until complete dissolving; another poor organic solvent [was] *is* then added slowly while being stirred, and the crystalline form A [was] *is* obtained by filtering and evaporating in the air; or Method 3: Crystalline form E of benfotiamine [was] *is* suspended in an organic solvent, followed by stirring in a hybrid oven for at least 24 h, and the crystalline form B then [was] *is* obtained by filtering and evaporating in the air; or Method 4: Crystalline form E of benfotiamine [was] *is* suspended in an organic solvent and the mixture [was] *is* heated to 60° C. while being stirred until complete dissolving; after the addition [was] *is* complete the mixture [was] *is* cooled in an ice bath, followed by stirring; and then the crystalline form C [was] *is* obtained by filtering and evaporating in the air; or Method 5: Crystalline form E of benfotiamine [was] *is* suspended in an organic solvent, followed by stirring using a magnetic stirrer for at least 24 h, and then the crystalline form D [was] *is* obtained by filtering and evaporating in the air.

18. The [process for preparing crystalline polymorphs of benfotiamine obtained by the] process of claim 17, wherein the organic solvent includes at least one member selected from the group [including] *consisting of* methanol, ethanol, isopropanol, pentanol, acetone, 2-butanone, tetrahydrofuran, nitromethane, acetonitrile, chloroform, dichloromethane, methyl tertbutyl ether and mixtures thereof.

19. A pharmaceutical composition comprising a therapeutically effective amount of crystalline benfotiamine according to claim 1 and at least one pharmaceutically acceptable excipient.

20. The pharmaceutical composition of claim 19, wherein excipients comprise at least one member selected from fillers, disintegrants, binders, lubricants and mixtures thereof.

21. The pharmaceutical composition of claim 20, wherein fillers comprise at least one member selected from starch, lactose, crystalline cellulose, dextrin, mannitol, oxidase, calcium sulfate and mixtures thereof.

22. The pharmaceutical composition of claim 20, wherein disintegrants comprise at least one member selected from carboxymethylcellulose and its salt, crosslinked carboxymethylcellulose and its salt, crosslinked polyvinylpyrrolidone, sodium carboxymethyl starch, low-substituted hydroxypropylcellulose and mixtures thereof.

23. The pharmaceutical composition of claim 20, wherein binders comprise at least one member selected from polyvinylpyrrolidone, hydroxypropyl methyl cellulose, starch slurry and mixtures thereof.

24. The pharmaceutical composition of claim 20, wherein lubricants comprise at least one member selected from magnesium stearate, calcium stearate and mixtures thereof.

* * * * *